US00PP15748P2

(12) United States Plant Patent
Olesen et al.

(10) Patent No.: US PP15,748 P2
(45) Date of Patent: May 3, 2005

(54) FLORIBUNDA ROSE PLANT NAMED 'POULCS016'

(50) Latin Name: *Rosa hybrida*
Varietal Denomination: POULcs016

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,761

(22) Filed: Mar. 29, 2004

(51) Int. Cl.[7] ..... A01H 5/00
(52) U.S. Cl. ..... Plt./149
(58) Field of Search ..... Plt./149

*Primary Examiner*—Kent Bell

(57) ABSTRACT

A new garden rose plant of the floribunda class which has abundant, deep pink flowers and attractive foliage. This new and distinct variety has shown to be uniform and stable in the resulting generations from asexual propagation.

2 Drawing Sheets

Botanical classification: *Rosa hybrida.*
Variety denomination: 'POULcs016'.

SUMMARY OF THE INVENTION

The present invention constitutes a new and distinct variety of garden rose plant which originated from a controlled crossing between the female parent, an un-named seedling, and the male parent plant, an un-named seedling. The two parents were crossed during the summer of 1993 and the resulting seeds were planted in a controlled environment in Fredensborg, Denmark. The new variety is named 'POULcs016'.

The new variety may be distinguished from its female seed parent by the following combination of characteristics:

1. While the seed parent has red flowers, 'POULcs016' has deep pink flowers.
2. 'POULcs016' are more compact and uniform than the female seed parent plant.

The new variety may be distinguished from its male pollen parent by the following combination of characteristics:

1. While the pollen parent is very compact, growing up to 60 cm in height, 'POULcs016' is less compact, reaching 80 cm in height.
2. While the pollen parent has light pink flowers, 'POULcs016' has deep pink flowers.

The objective of the hybridization of this rose variety was to create a new and distinct variety for garden use with unique qualities, such as:

1. Uniform and abundant deep pink flowers;
2. Vigorous, but compact growth when propagated both as a budded rose and on its own roots;
3. Disease resistance;
4. Continuous flowering.

This combination of qualities is not present in previously available commercial cultivars of this type, known to the inventors, and distinguish 'POULcs016' from all other varieties of which we are aware.

As part of their rose development program, L. Pernille Olesen and Mogens N. Olesen germinated the seeds from the aforementioned hybridization during winter of 1993 and conducted evaluations on the resulting seedlings in a controlled environment in Fredensborg, Denmark.

'POULcs016' was selected in the spring 1994 by the inventors as a single plant from the progeny of the aforementioned hybridization.

Asexual reproduction of 'POULcs016' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULcs016' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs016'. Specifically illustrated in SHEET 1:

FIG. 1.1; Open flowers, one showing a peduncle;

FIG. 1.2; Flower bud closed, flower bud as sepals unfold, and partially open;

FIG. 1.3; Flower petals, detached;

FIG. 1.4; Sepals, receptacle, and peduncle;

Specifically illustrated in SHEET 2:

FIG. 2.1; Juvenile growth exhibiting anthocyanin and flower bud;

FIG. 2.2; Stems exhibiting thorns;

FIG. 2.3; Leaves.

DETAILED DESCRIPTION OF THE VARIETY

The following is a description of 'POULcs016', as observed in its growth in a field nursery in Jackson County, Oreg. Observed plants are 3 years of age. Plants were grown on *Rosa multiflora* understock. Color references are made using The Royal Horticultural Society (London, England) Colour Chart, 1995, except where common terms of color are used.

For a comparison, several physical characteristics of the rose variety 'Poulbella', a rose variety from the same inventors described and illustrated in U.S. Plant Pat. No. 12,904 issued Sep. 3, 2002 are compared to 'POULcs016' in Chart 1.

CHART 1

| | 'POULcs016' | 'POULbella' |
|---|---|---|
| General Tonality | Red-Purple Group 57C | Red-Purple Group 57C |
| Petalage | 25 petals | 35 to 40 |
| Filament Color | Yellow Group 13A | Red Group 51A |

FLOWER AND FLOWER BUD

Blooming habit: Continuous.

Flower bud:

*Size.*—Upon opening, 20 mm in length from base of receptacle to end of bud. Bud diameter is 13 mm on average.

*Bud form.*—Pointed ovoid.

*Bud color.*—As sepals unfold, petals are Red Group 46B. At ¼ opening petals are Red-Purple Group 57B.

*Sepals.*—Upper Surface: Color: Green Group 138B. Surface: Strongly pubescent. Lower Surface: Color: Yellow-Green Group 144A. Anthocyanic pigments the color of Greyed-Red Group 178A observed. Sepal Shape: Sepal apex is cirrhose. Base is flat at union with receptacle. Sepal Margin: Margins have weak foliaceous appendages on three of the five sepals. Stipitate glands are scant. Size: 30 mm×(l)×11 mm (w).

*Receptacle.*—Texture: Smooth and glaucous. Shape: Funnel shaped. Size: 9 mm (h)×8 mm (w). Color: Yellow-Green Group 144A. Anthocyanic pigments the color of Greyed-Red Group 178B observed.

*Peduncle.*—Surface: Smooth. Few stipitate glands. Length: 15 to 35 mm. Color: Yellow-Green Group 144B. Anthocyanic pigments the color of Greyed-Red Group 178B observed. Strength: Somewhat strong.

*Borne.*—In clusters of 7 flower buds per stem.

Flower bloom:

*Fragrance.*—Moderate floral scent.

*Duration.*—The blooms have a duration on the plant of approximately 10 to 14 days. Petals fall cleanly away from plant.

*Size.*—Flower diameter is 70 mm when open.

*Form.*—General shape is a reflexed open cup. Shape of flower when viewed from the side: Upon opening: Upper portion: Flat. Lower portion: Flat. Open flower; Upper portion: Flat. Lower portion: Concave.

Petalage: 25 petals under normal conditions with 4 petaloids.

Color:

Upon opening, petals:

*Outermost petals.*—Outer side: Red-Purple Group 57C. Inner Side: Red-Purple Group 57C.

*Innermost petals.*—Outer side: Red-Purple Group 57C. Inner Side: Red-Purple Group 58C.

Upon opening, basal petal spots:

*Outermost petals.*—Outer side: Yellow Group 7C. Inner Side: Yellow Group 7C.

*Innermost petals.*—Outer side: Yellow Group 7C. Inner Side: Yellow Group 7C.

After opening, petals:

*Outermost petals.*—Outer side: Red-Purple Group 57C. Inner Side: Red-Purple Group 57C.

*Innermost petals.*—Outer side: Red-Purple Group 57C. Inner Side: Red-Purple Group 57C.

After opening: No distinctive coloration at the petal base observed.

General tonality: On open flower Red-Purple Group 57C. No change in the general tonality at the end of the $10^{th}$ day.

Petals:

*Petal reflex.*—Slightly reflexed.

*Margin.*—Entire and uniform. Weak undulations of margin observed.

*Shape.*—Generally deltoid. Apex is rounded. Base is acute.

*Size.*—40 mm (l)×40 mm (w).

*Texture.*—Smooth.

*Thickness.*—Thick.

*Arrangement.*—Not Formal.

Petaloids:

*Quantity.*—3 to 5.

*Color.*—Upper Surface: Red-Purple Group 57C. Lower Surface: Red-Purple Group 57C.

*Size.*—22 mm (l)×15 mm (w).

*Shape.*—Elliptical.

Reproductive organs:

*Pistils.*—Length: 6 mm. Quantity: 70 (actual count).

*Pollen.*—None Observed.

*Anthers.*—Size: 2 mm in length. Color: Yellow-Orange Group 15A. Quantity: 130 (actual count).

*Filaments.*—Color: Yellow Group 13A. Length: 8 mm.

*Stigmas.*—Inferior relative to the length of the filaments and height of the anthers. Color: Yellow-Green Group 150D.

*Styles.*—Color: Yellow-Green Group 150D.

*Hips.*—None Observed in the field nursery in Jackson County, Oreg.

PLANT

Plant growth: Moderate, upright to bushy. When grown as a budded field grown plant on *Rosa multiflora* understock, the average height of the plant is 80 cm and the average width is 70 cm.

Stems:

*Color.*—Young wood is Yellow-Green Group 144B with intonations of Greyed-Red Group 178A. Older wood is Yellow-Green Group 144B with intonations of Greyed-Red Group 178A.

*Surface texture.*—Young wood: Smooth. Older wood: Smooth.

Thorns:

*Incidence.*—15 thorns per 10 cm of stem.

*Size.*—Average length: 5 mm.

*Color.*—Greyed-Red Group 179A.

*Shape.*—Concave.

Plant foliage: Normal number of leaflets on normal leaves in middle of the stem: 7 leaflets.

*Compound leaf size.*—80 to 120 mm (l)×55 to 80 mm (w).

*Color.*—Mature Foliage: Upper surface is: Yellow-Green Group 146A. Lower surface is: Yellow-Green Group 146B. Juvenile foliage: Upper surface is: Yellow-Green Group 146B. Lower surface is: Yellow-Green Group 146B with intonations of Greyed-Red Group 178A. Anthocyanin: Location:

Juvenile shoots and leaves. Color: Greyed-Red Group 178A.

Plant leaves and leaflets:

*Stipules.*—Size: 18 mm in length. Quantity: 2 per compound leaf. Margins: Finely serrated with stipitate glands. Color: Yellow-Green Group 144A.

*Petiole.*—Length: 32 mm. Above: Color: Yellow-Green Group 144C with anthocyanic pigments on the upper surface the color of Greyed-Red Group 179A. Underneath: Observations: Thorns and stipitate glands observed.

*Rachis.*—Length: 50 mm. Above: Color: Yellow-Green Group 144C with anthocyanic pigments on the upper surface the color of Greyed-Red Group 179A. Underneath: Observations: Thorns and stipitate glands observed.

*Leaflet.*—Size: 45 mm (l)×40 mm (w). Edge: Serrated. Shape: Generally rounded. Apex is mucronate. Base is rounded. Thickness: Thick. Arrangement: Odd pinnate. Venation: Reticulate. Texture: Smooth. Glossiness: Moderately glossy.

Disease resistance: Above average resistance to mildew, rust, black spot, and *Botrytis* under normal growing conditions in Jackson County, Oreg.

Cold hardiness: The variety 'POULcs016' has been found to be cold tolerant to USDA Cold Hardiness Zone 6.

It is claimed:

1. A new and distinct variety of rose plant of the floribunda rose class, substantially as herein illustrated and described as a distinct and novel rose variety due to its abundant deep pink flowers, disease resistance, and extended period of bloom.

* * * * *

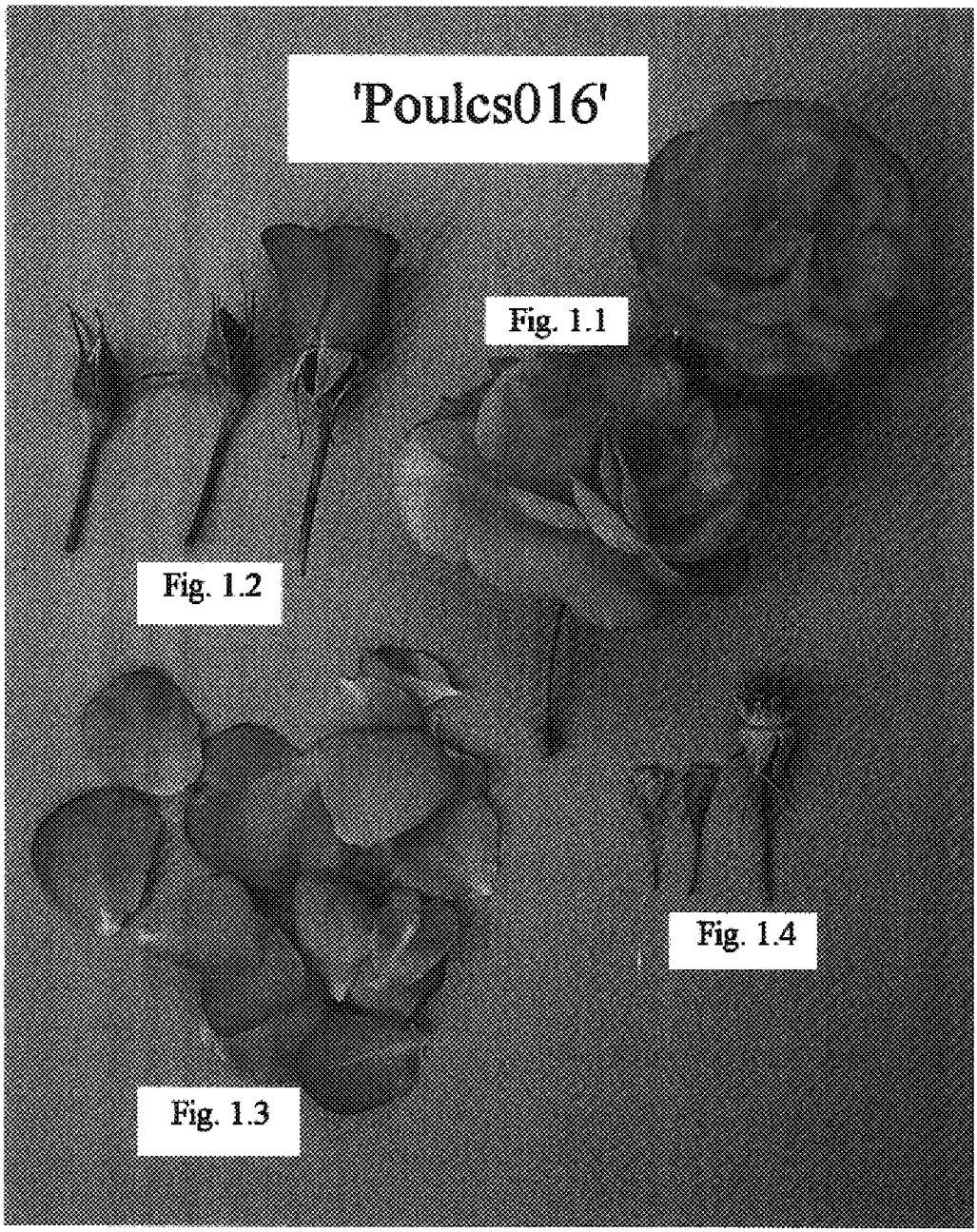
'Poulcs016'
Fig. 1.1
Fig. 1.2
Fig. 1.3
Fig. 1.4

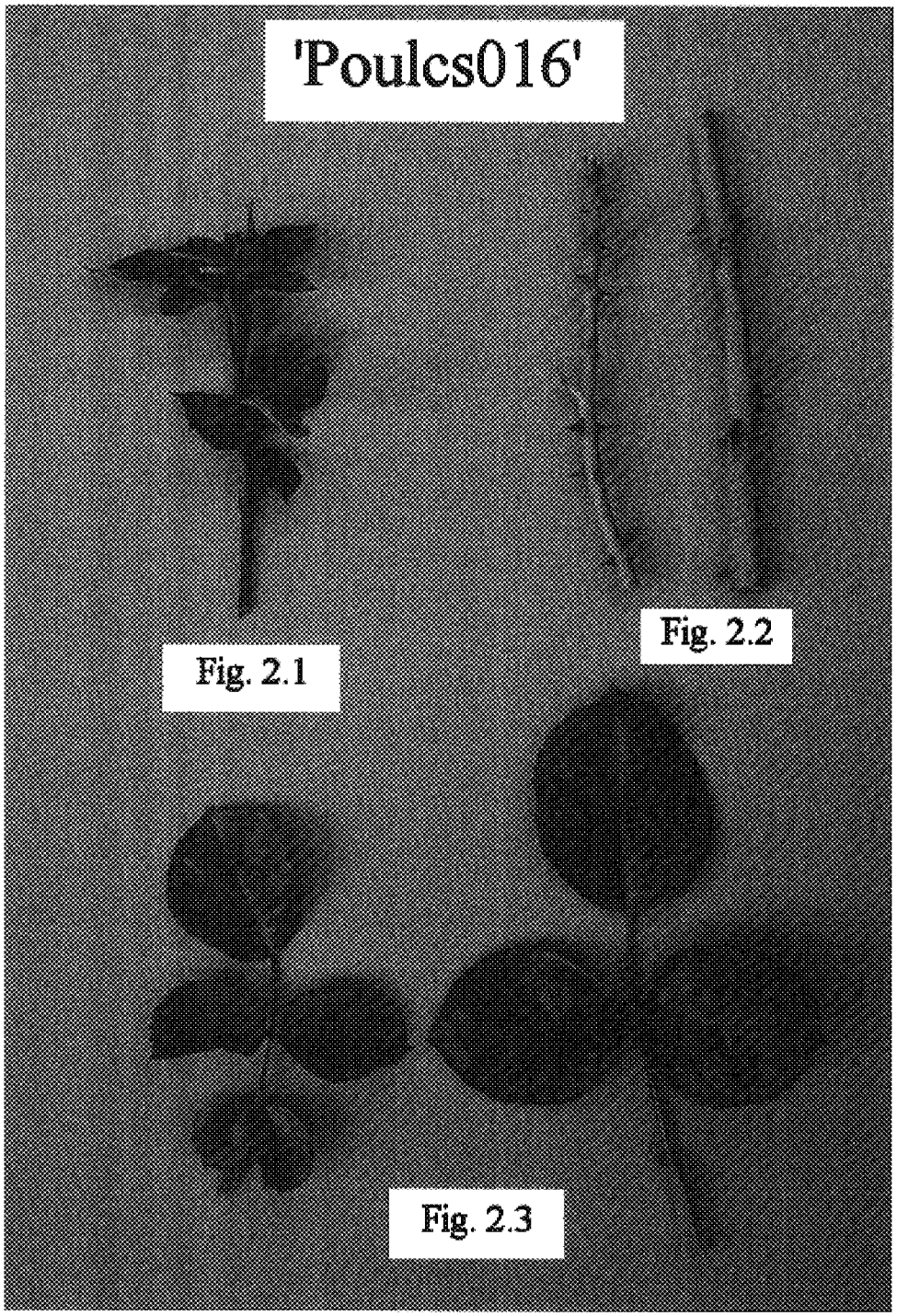
'Poulcs016'
Fig. 2.1
Fig. 2.2
Fig. 2.3